United States Patent [19]
Maurin et al.

[11] Patent Number: 6,156,297
[45] Date of Patent: Dec. 5, 2000

[54] CONDITIONING AND DETERGENT COMPOSITIONS AND USE

[75] Inventors: Véronique Maurin, Paris; Myriam Mellul, L'Hay les Roses; Bernard Beauquey, Clichy, all of France

[73] Assignee: L'Oreal, S.A., Paris, France

[21] Appl. No.: 09/338,864

[22] Filed: Jun. 23, 1999

[30] Foreign Application Priority Data

Jun. 24, 1998 [FR] France ................................ 98 08007

[51] Int. Cl.⁷ ................................ A61K 7/08; A61K 7/02
[52] U.S. Cl. ................ 424/70.19; 424/70.1; 424/70.21; 424/70.22; 424/70.24; 424/70.31; 424/59
[58] Field of Search ...................... 424/59, 70.1, 70.19, 424/70.21, 70.22, 70.24, 70.31

[56] References Cited

U.S. PATENT DOCUMENTS

| | | |
|---|---|---|
| 2,528,378 | 10/1950 | Mannheimer . |
| 2,781,354 | 2/1957 | Mannheimer . |
| 4,963,535 | 10/1990 | Sebag et al. . |
| 5,324,507 | 6/1994 | Dubief et al. . |
| 5,510,100 | 4/1996 | Picard et al. . |

FOREIGN PATENT DOCUMENTS

| | | |
|---|---|---|
| 0 337 354 | 10/1989 | European Pat. Off. . |
| 0 498 716 | 8/1992 | European Pat. Off. . |
| 0 589 407 | 3/1994 | European Pat. Off. . |
| 0 628 305 | 12/1994 | European Pat. Off. . |
| 0 629 396 | 12/1994 | European Pat. Off. . |
| 0 681 832 | 11/1995 | European Pat. Off. . |
| 2 270 846 | 12/1975 | France . |
| 2 383 660 | 10/1978 | France . |
| 2 470 596 | 6/1981 | France . |
| 2 519 863 | 7/1983 | France . |
| 2 598 611 | 11/1987 | France . |
| 2 663 847 | 1/1992 | France . |
| 41 39 935 | 6/1993 | Germany . |
| 44 05 127 | 8/1995 | Germany . |
| 195 11 637 | 10/1996 | Germany . |
| 195 43 633 | 5/1997 | Germany . |
| 6-287595 | 10/1994 | Japan . |
| 9-175936 | 7/1997 | Japan . |
| WO 92/06669 | 4/1992 | WIPO . |
| WO 93/19149 | 9/1993 | WIPO . |
| WO 93/23512 | 11/1993 | WIPO . |
| WO 94/03150 | 2/1994 | WIPO . |
| WO 94/16677 | 8/1994 | WIPO . |
| WO 95/06702 | 3/1995 | WIPO . |
| WO 95/22312 | 8/1995 | WIPO . |
| WO 96/25144 | 8/1996 | WIPO . |
| WO 96/28140 | 9/1996 | WIPO . |
| WO 96/37285 | 11/1996 | WIPO . |

OTHER PUBLICATIONS

English language Derwent Abstract of DE 41 39 935.
English language Derwent Abstract of EP 0 498 716.
English language Derwent Abstract of EP 0 681 832.
English language Derwent Abstract of FR 2 270 846.
English language Derwent Abstract of FR 2 383 660.
English language Derwent Abstract of FR 2 663 847.
English language Derwent Abstract of JP 9–175936.
English language Derwent Abstract of JP 6–287595.
English language Derwent Abstract of DE 44 05 127.
English language Derwent Abstract of DE 195 11 637.
English language Derwent Abstract of DE 195 43 633.
English language Derwent Abstract of EP 0 628 305.
English language Derwent Abstract of FR 2 470 596.
English language Derwent Abstract of FR 2 519 863.
English language Derwent Abstract of FR 2 598 611.

Primary Examiner—Thurman K. Page
Assistant Examiner—P. M. Queeney
Attorney, Agent, or Firm—Finnegan, Henderson, Farabow, Garrett & Dunner, L.L.P.

[57] ABSTRACT

The present invention relates to a conditioning and detergent cosmetic composition for keratinous substances comprising, in an aqueous medium:
(A) at least one non-volatile vegetable oil,
(B) at least one anionic sulphate surface-active agent,
(C) at least one non-ionic alkyl glycoside surface-active agent, the (B)/(C) ratio by weight being less than or equal to 2:1.

Use in simultaneously caring for and washing keratinous substances, in particular the hair.

30 Claims, No Drawings

CONDITIONING AND DETERGENT COMPOSITIONS AND USE

The present invention relates to cosmetic compositions which are both conditioning and detergent for the simultaneous care and washing of keratinous substances. The invention also relates to the use of these compositions in the abovementioned application.

Detergent (shampoo or shower gel) compositions based essentially on conventional surface-active agents of, in particular, anionic, non-ionic and/or amphoteric type, but more particularly of anionic type, are used for cleaning and/or washing the hair and/or skin. These compositions are applied to wet hair or skin and the foam generated by massaging or rubbing with the hands makes it possible, after rinsing with water, to remove dirt initially present on the hair or the skin.

Although having good washing power, these base compositions possess cosmetic properties that remain fairly weak, in particular because the relatively aggressive nature of such a cleaning treatment can result, in the long term, in more or less marked damage to the keratinous substances, damage related in particular to the gradual removal of the lipids or proteins present in or at the surface of these keratinous substances.

Consequently, in order to improve the cosmetic properties of the above detergent compositions and more particularly of those which are required to be applied to sensitized hair (i.e. hair which is damaged or embrittled, in particular under the chemical action of atmospheric agents and/or hair treatments, such as permanent waves, dyeings or bleachings), additional cosmetic agents, known as conditioners, intended mainly to repair or limit the harmful or undesirable effects brought about by the various treatments or attacks to which hair fibers are more or less repeatedly subjected, are introduced into these detergent compositions. These conditioners can also improve the cosmetic behavior of natural hair. The most commonly used conditioners in shampoos are cationic polymers, silicones and/or silicone derivatives. These types of conditioners confer, on washed, dry or wet hair, an ease of disentangling, a softness and a smoothing which are increased with respect to what can be obtained with the corresponding cleaning compositions which are devoid of them.

Despite the progress recently achieved in the field of shampoos based on silicone and cationic polymers, these do not really completely give satisfaction, so that a strong need still currently exists with regard to being able to have available novel products exhibiting better performances with regard to one or more of the cosmetic properties mentioned above. Provision has already been made to use vegetable or animal oils as conditioner. However, conventional compositions have unsatisfactory detergent and foaming properties. Furthermore, the keratinous substances treated with these compositions often exhibit an unacceptable greasy feel.

An object of the present invention is to provide conditioning and detergent compositions which are sufficiently foaming and which exhibit good conditioning properties, in particular disentangling, softness and sheen properties, without conferring a greasy nature.

After much research directed at this question, the inventors have now discovered, entirely unexpectedly and surprisingly, that, by combining a non-volatile vegetable oil, an anionic surfactant of sulphate type and a non-ionic surface-active agent chosen from the alkyl glycoside group, it is possible to obtain detergent compositions which can exhibit excellent cosmetic properties, in particular of disentangling, of softness and of sheen and of body of the keratinous substances treated, while retaining their good intrinsic washing power and their foaming power.

These novel compositions can make it possible to deposit a larger amount of oil on keratinous substances (in particular the hair) than with a conventional composition but without a greasy feel or visual appearance.

The compositions in accordance with the invention can confer on keratinous substances, in particular the hair, a noteworthy treating effect which is revealed in particular by an ease of disentangling, as well as a contribution of body, of lightness, of smoothing, of softness and of suppleness and of manageability without any feeling of greasiness.

One aspect of the present invention is thus novel conditioning and detergent foaming cosmetic compositions comprising, in an aqueous medium:
(A) at least one non-volatile vegetable oil,
(B) at least one anionic sulphate surface-active agent,
(C) at least one non-ionic alkyl glycoside surface-active agent, the (B)/(C) ratio by weight being less than or equal to 2:1.

Another aspect of the present invention is the use of the compositions according to the invention for simultaneously caring for and washing keratinous substances, such as the hair and the skin.

A detailed description of preferred embodiments of the present invention will now be given.

According to the invention, the (B)/(C) ratio by weight is preferably from 0.1:1 to 1.8:1, more preferably from 0.5:1 to 1.7:1 and more preferably still from 1:1 to 1.5:1.

The non-volatile vegetable oils which can be used in the compositions of the invention are optionally hydrogenated natural oils which are generally insoluble in water. The vegetable oils generally do not comprise fatty acid mono- or diglycerides, but if present, such fatty acid mono- or diglycerides preferably comprise less than 2% by weight with respect to the weight of the oil.

A non-volatile vegetable oil according to the invention is an oil which exhibits a boiling temperature generally greater than 300° C. at 760 mm of Hg (101,325 Pa) and which does not exhibit or which exhibits a very low vapor pressure. In particular, essential oils, which are volatile oils, are not within the definition of vegetable oils according to the invention.

The vegetable oils according to the present invention are preferably chosen from sunflower oil, avocado oil, jojoba oil, maize oil, sweet almond oil, soybean oil, cucumber oil, grape seed oil, sesame oil, hazelnut oil, palm oil, castor oil, walnut oil, cashew nut oil and purcellin oil. More preferably, the vegetables oils are chosen from the oils resulting from dicotyledonous plants, such as avocado oil and jojoba oil.

The anionic surfactants of sulphate type are at least one salt chosen from salts of alkyl sulphates, alkyl ether sulphates, alkylamido ether sulphates, alkylaryl ether sulphates and alkyl ether sulphosuccinates. The salts are preferably chosen from alkali metal salts, ammonium salts, amine salts, aminoalcohol salts,and magnesium salts. The alkali metal salts are preferably sodium salts. The alkyl radical in all these various compounds preferably comprises from 8 to 24 carbon atoms and the aryl radical preferably is chosen from phenyl and benzyl groups. However, the mean number of ethylene oxide or propylene oxide groups can preferably range from 2 to 50 and more particularly from 2 to 10.

The anionic surfactants are preferably at least one salt chosen from the salts of alkyl sulphates and the salts of alkyl ether sulphates. More preferably, the at least one salt is chosen from $C_8$–$C_{14}$, and more preferably $C_{12}$–$C_{14}$, alkyl ether sulphate salts.

These salts preferably comprise from 2 to 5 ethylene oxide groups. Preferably, the anionic surfactant is an anionic surface-active agent chosen from oxyethylenated sodium, triethanolamine and ammonium ($C_{12}$–$C_{14}$)alkyl ether sulphates comprising approximately 2.2 mol of ethylene oxide.

The non-ionic surface-active agent or agents of alkyl glycoside type used in the context of the present invention are products which are well known per se and they can be more particularly represented by the following general formula (I):

  (I)

in which:

R$_1$ is chosen from linear and branched, saturated and unsaturated, alkyl radicals comprising approximately from 8 to 24 carbon atoms and alkylphenyl radicals in which the linear and branched alkyl radicals comprise approximately from 8 to 24 carbon atoms;

R$_2$ is chosen from alkylene radicals comprising from 2 to 4 carbon atoms;

G is chosen from reduced sugars comprising from 5 to 6 carbon atoms;

t ranges from 0 to 10; and, v ranges from 1 to 15.

Preferred alkyl glycosides according to the present invention are compounds of formula (I) in which: R$_1$ is preferably chosen from saturated and unsaturated, linear and branched alkyl radicals comprising from 8 to 14 carbon atoms; t ranges from 0 to 3 and more preferably is 0; and G is chosen from glucose, fructose, and galactose, preferably glucose. The degree of polymerization (S) of the saccharide, i.e. the value of v in the formula (I), can range from 1 to 15. According to the invention, preference is given to reduced sugars comprising 80% or more of sugars for which the degree of polymerization (S) ranges from 1 to 4. The mean degree of polymerization is more particularly from greater than 1 to 2.

Compounds of formula (I) are represented in particular by the products sold by the company Henkel under the name APG, such as the products APG 300, APG 350, APG 500, APG 550, APG 625 or APG base 10–12, or under the names Plantaren (1200 and 2000) or Plantacare (818, 1200 and 2000). Use may also be made of the products sold by the company SEPPIC under the names Triton CG 110 (or Oramix CG 110) and Triton CG 312 (or Oramix NS 10), the products sold by the company BASF under the name Lutensol GD 70 or those sold by the company Chem Y under the name AG10 LK.

It is also possible, according to the invention, to combine a surface-active agent of amphoteric type with the two types of surfactants described above.

The amphoteric surface-active agents are preferably chosen from:

aliphatic, secondary, and tertiary amine derivatives, wherein the aliphatic radical is chosen from linear and branched chains comprising from 8 to 18 carbon atoms and further wherein the radical comprises at least one water-solubilizing anionic group (for example carboxylate, sulphonate, sulphate, phosphate or phosphonate), ($C_8$–$C_{20}$)alkyl betaines, ($C_8$–$C_{20}$)alkyl sulphobetaines, ($C_8$–$C_{20}$)alkyl amido($C_1$–$C_6$)alkyl betaines and ($C_8$–$C_{20}$)alkyl amido($C_1$–$C_6$)alkyl sulphobetaines.

Mention may be made, among amine derivatives, of the products sold under the name Miranol®, as disclosed in U.S. Pat. Nos. 2,528,378 and 2,781,354, the disclosures of both of which are incorporated by reference herein, and with structures:

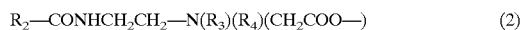  (2)

in which: R$_2$ is chosen from alkyl radicals derived from R$_2$—COOH acids present in hydrolysed coconut oil, and heptyl, nonyl, and undecyl radicals, R$_3$ is a β-hydroxyethyl group and R$_4$ is a carboxymethyl group; and

  (3)

in which:

D represents —CH$_2$CH$_2$OX', E represents —(CH$_2$)$_Z$—Y', with Z=1 or 2,

X' is chosen from a —CH$_2$CH$_2$—COOH group and a hydrogen atom,

Y' is chosen from —COOH and a —CH$_2$—CHOH—SO$_3$H radical,

R$_{2'}$ is chosen from radicals derived from acids present in hydrolysed linseed oil and coconut oil, alkyl radicals, preferably $C_7$, $C_9$, $C_{11}$ and $C_{13}$ alkyl radicals, a $C_{17}$ alkyl radical and its iso form, and unsaturated $C_{17}$ radicals.

These compounds are classified in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphodipropionate, Disodium Caprylamphodipropionate, Disodium Capryloamphodipropionate, Lauroamphodipropionic acid, Cocoamphodipropionic acid, and the descriptions therein are incorporated by reference herein.

Mention may be made, as an example, of the cocoamphodiacetate sold under the tradename Miranol® C2M concentrate by the Rhône-Poulenc.

According to the present invention, it is more preferable to use the amphoteric surface-active agents belonging to the group of the betaines, such as the alkyl betaines, in particular the cocoyl betaine sold under the name "Dehyton AB 30" as a 30% aqueous solution of AM by the company Henkel, or the alkyl amido betaines, such as Tegobetaine® F50, sold by the company Goldschmidt.

According to the invention, the composition can also comprise anionic surfactants chosen from phosphates, sulphonates and carboxylates. These anionic surfactants are preferably chosen from alkyl sulphonates, alkyl phosphates, alkylamide sulphonates, alkylaryl sulphonates, α-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; alkyl sarcosinates; acyl isethionates and N-acyltaurates, the alkyl or acyl radical of all these various compounds preferably comprising from 12 to 20 carbon atoms and the aryl radical preferably being chosen from phenyl and benzyl groups. More preferably, the anionic surfactants are alkyl D-galactoside uronic acids and their salts, as well as polyoxyalkylenated ($C_6$–$C_{24}$)alkyl ether carboxylic acids, polyoxyalkylenated ($C_6$–$C_{24}$)alkylaryl ether carboxylic acids, polyoxyalkylenated ($C_6$–$C_{24}$) alkylamido ether carboxylic acids and their salts, in particular those comprising from 2 to 50 ethylene oxide groups, and their mixtures.

The anionic surface-active agent(s) of sulphate type are generally present in a proportion from 1 to 20% by weight, preferably from 3 to 15% by weight, with respect to the total weight of the composition.

The non-ionic surface-active agent(s) of alkyl glycoside type are generally present in a proportion from 0.5 to 15%, preferably from 1 to 10%, by weight with respect to the total weight of the composition.

The amphoteric surface-active agent(s) are generally present in a proportion from 0.5 to approximately 10% by weight, preferably from 1 to 5% by weight, with respect to the total weight of the composition.

When they are present, the amphoteric surfactants can represent approximately less than 30% by weight of the combined anionic surfactants and alkyl glycosides.

When they are present, the anionic surfactants chosen from phosphate, sulphonate and carboxylates can preferably represent approximately less than 30% by weight of the combined anionic surfactants.

The anionic surfactants/alkyl glycosides ratio by weight is generally less than or equal to 2:1.

In the composition according to the present invention, the combined detergent surfactants generally range from 3 to 50% by weight and preferably from 5 to 30% by weight with respect to the total weight of the composition.

The non-volatile vegetable oil or oils are preferably used in the compositions in accordance with the invention in concentrations of less than 20% by weight and generally in concentrations from 0.1 to 20%, preferably from 0.2 to 10% by weight and more preferably from 1 to 8% by weight with respect to the total weight of the composition.

The cosmetically acceptable aqueous medium can be composed solely of water or of a mixture of water and of a cosmetically acceptable solvent, such as a lower $C_1$–$C_4$ alcohols or such as alkylene glycols. The lower $C_1$–$C_4$ alcohols are preferably chosen from ethanol, isopropanol, tert-butanol, and n-butanol. The alkylene glycols are preferably chosen from propylene glycol and glycol ethers.

The detergent compositions according to the invention exhibit a final pH generally from 3 to 10. This pH is preferably from 5 to 8. The pH can be conventionally adjusted to the desired value by addition of a base (organic or inorganic) to the composition, for example sodium hydroxide, ammonia or a primary, secondary or tertiary (poly)amine, such as monoethanolamine, diethanolamine, triethanolamine, isopropanolamine or 1,3-propanediamine, or by addition of acid, preferably a carboxylic acid, such as, for example, citric acid.

The compositions in accordance with the invention can comprise viscosity-regulating agents, such as electrolytes, or thickening agents, in addition to the combination defined above. Mention may in particular be made of sodium chloride, sodium xylenesulphonate, scleroglucans, xanthan gums, fatty acid alkanolamides, alkyl ether carboxylic acid alkanolamides optionally oxyethylenated with up to 5 mol of ethylene oxide, such as the product sold under the name "Aminol A 15" by the company Chem Y, crosslinked polyacrylic acids and crosslinked acrylic acid/$C_{10}$–$C_{30}$ alkyl acrylate copolymers. These viscosity-regulating agents are used in the compositions according to the invention in proportions which can preferably range up to 10% by weight with respect to the total weight of the composition.

The compositions in accordance with the invention can also preferably comprise up to 5% of pearlescent or opacifying agents well known in the state of the art, such as, for example, sodium palmitate, magnesium palmitate, sodium stearate, sodium hydroxystearate, magnesium stearate, magnesium hydroxystearate, acylated derivatives comprising a fatty chain, such as ethylene glycol monostearate, ethylene glycol distearate, polyethylene glycol monostearate or polyethylene glycol distearate, fatty alcohols, or ethers comprising fatty chains, such as, for example, distearyl ether or 1-(hexadecyloxy)-2-octadecanol.

The compositions in accordance with the invention can optionally comprise, in addition, other agents having the effect of improving the cosmetic properties of hair or the skin, without, however, detrimentally affecting the stability and/or the washing and foaming properties of the compositions. Mention may be made, in this respect, of cationic surface-active agents, anionic or non-ionic or cationic or amphoteric polymers, proteins, protein hydrolysates, ceramides, pseudoceramides, fatty acids comprising linear or branched $C_{16}$–$C_{40}$ chains, such as 18-methyleicosanoic acid, hydroxy acids, vitamins, panthenol, fatty acid esters, volatile or non-volatile silicones which are soluble and insoluble in the medium, moisturizing agents, antidandruff or antiseborrhoeic agents, sunscreening agents, agents for combating free radicals, mineral oils, synthetic organic oils and their mixtures.

The total amount of lipophilic compounds, such as, for example, the vegetable oils according to the invention, silicones or mineral oils, is generally less than 20% by weight with respect to the total weight of the composition.

The cationic polymers which can be used in accordance with the present invention can be chosen from all those already known per se as improving the cosmetic properties of hair treated with detergent compositions, namely in particular those disclosed in Patent Application EP-A-0,337, 354 and in French Patent Applications FR-A-2,270,846, 2,383,660, 2,598,611, 2,470,596 and 2,519,863, the disclosure of each of which is herein incorporated by reference.

More generally still, within the meaning of the present invention, the expression "cationic polymer" denotes any polymer comprising cationic groups and/or groups which can be ionized to cationic groups.

Preferably the cationic polymers in accordance with present invention, are quaternary cellulose ether derivatives, such as the products sold under the name "JR 400" by the company Union Carbide Corporation, cyclopolymers, in particular diallyldimethylammonium salt homopolymers and diallyldimethylammonium salt and acrylamide copolymers, in particular the chlorides, sold under the names "Merquat 100", "Merquat 550" and "Merquat S" by the company Merck, cationic polysaccharides and more particularly guar gums modified by 2,3-epoxypropyltrimethylammonium chloride, sold, for example, under the name "Jaguar C13S" by the company Meyhall, or optionally crosslinked homopolymers and copolymers of (meth)acryloyloxyethyltrimethylammonium salt, sold by the company Allied Colloids as a 50% solution in mineral oil under the tradenames Salcare SC92 (crosslinked copolymer of methacryloyloxyethyltrimethylammonium chloride and of acrylamide) and Salcare SC95 (crosslinked homopolymer of methacryloyloxyethyltrimethylammonium chloride). Use may also be made of the polymers which are composed of repeat units corresponding to the formula:

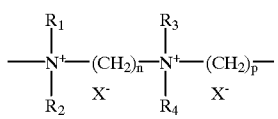

in which $R_1$, $R_2$, $R_3$ and $R_4$, which are identical or different, are chosen from alkyl and hydroxyalkyl radicals having from 1 to 4 carbon atoms approximately, n and p are integers ranging from 2 to 20 approximately and $X^-$ is an anion selected from anions derived from inorganic and organic acids.

A particularly preferred compound of formula (a), known as Hexadimethrine chloride under the INCI (CTFA) nomenclature, is that in which $R_1$, $R_2$, $R_3$ and $R_4$ are each a methyl radical and n=3, p=6 and X=Cl.

According to the invention, the cationic polymer or polymers can preferably range from 0.001% to 10% by weight, preferably from 0.005% to 5% by weight and more preferably still from 0.01% to 3% by weight of the total weight of the final composition.

The compositions according to the invention can also comprise foam synergists, such as $C_{10}$–$C_{18}$ 1,2-alkanediols or fatty alkanolamides derived from mono- or from diethanolamine.

Of course, a person skilled in the art will take care to choose this or these optional additional compounds and/or their amounts so that the advantageous properties of the combination in accordance with the invention are not, or not substantially, detrimentally affected by the envisaged addition or additions.

The foaming power of the compositions according to the invention, characterized by foam height, is generally greater than 75 mm; preferably, greater than 100 mm, measured according to the modified Ross-Miles method (NF T 73-404/ISO696).

The modifications to the method are as follows: The measurement is carried out at a temperature of 22° C. with water purified by osmosis. The concentration of the solution is 2 g/l. The height of the drop is 1 m. The amount of composition which drops is 200 ml. These 200 ml of composition fall into a measuring cylinder having a diameter of 50 mm and comprising 50 ml of the composition to be tested. The measurement is taken 5 minutes after the composition has finished being run in.

These compositions can be provided in the form of more or less thick liquids, of creams or of gels and they are mainly suitable for washing and caring for the hair.

When the compositions according to the invention are employed as shampoos, they are simply applied to wet hair and the foam generated by massaging or friction with the hands is subsequently removed, after an optional resting time, by rinsing with water, it being possible for the operation to be repeated one or more times.

Another subject-matter of the invention is a process for washing and conditioning keratinous substances, such as, in particular, the hair, which comprises applying, to the said wet substances, an effective amount of a composition as defined above and in then rinsing with water, after an optional resting time.

The compositions in accordance with the invention can also be used as shower gels, foam baths or as foaming make-up removal products for washing and conditioning the hair and/or the skin, in which case they are applied to the wet skin and/or hair and are rinsed after application.

Concrete but in no way limiting examples illustrating the invention will now be given.

EXAMPLE 1

Two shampoo compositions were prepared, one in accordance with the invention (composition A) and the other comparative (composition B): (AM means Active Material):

|  | A | B |
| --- | --- | --- |
| ($C_8$/$C_{10}$/$C_{12}$/$C_{14}$)Alkyl polyglycoside-(1.4) as a 53% aqueous solution (APG) (Plantacare 2000 from Henkel) | 5.7 g AM | 3.5 g AM |
| Sodium lauryl ether sulphate oxyethylenated with 2.2 mol of ethylene oxide as an aqueous solution comprising 70% of AM | 11.5 g AM | 13.7 g AM |
| Avocado oil | 6 g | 6 g |
| Preservatives | q.s. | q.s. |
| Citric acid.1H2O q.s | pH 5.5 | pH 5.5 |
| Demineralized water q.s. for | 100 g | 100 g |

In the composition A, the surfactant of sulphate type/APG ratio is equal to 2:1.

In the composition B (comparative), the surfactant of sulphate type/APG ratio is equal to 4:1.

In both compositions, the total amount of surfactants is identical: 17.2 g.

Shampooing was carried out by applying approximately 12 g of the composition A to prewetted sensitized hair. The shampoo was made to foam and copious rinsing with water was then carried out.

The same procedure as above was carried out with the comparative composition B.

A panel of experts evaluated the foam of the two shampoos.

The starting of the foam was faster with the composition according to the invention (A). The amount of foam developed during application was greater with the composition A and the foam has more consistency.

A panel of experts evaluated the appearance of the dried hair.

All the experts indicated that the hair treated with the composition A according to the invention was more supple, more shiny and better behaved than the hair treated with the composition B.

EXAMPLE 2

A shampoo composition according to the invention was prepared with the following composition (AM means Active Material):

| (C8/C10/C12/C14)Alkyl polyglycoside-(1.4) as an aqueous solution comprising 53% of AM (Plantacare 2000 from Henkel) | 7.4 g AM |
| --- | --- |
| Sodium lauryl ether sulphate oxyethylenated with 2.2 mol of ethylene oxide as an aqueous solution comprising 70% of AM | 9.8 g AM |
| Avocado oil | 6 g |
| Preservatives | q.s. |
| Citric acid.1H2O q.s | pH 5.5 |
| Demineralized water q.s. for | 100 g |

Hair was washed using this composition. It was subsequently rinsed with running water.

Before drying, it is found that the hair is very soft in the wet state and satisfactorily disentangles. After drying, it is found that the hair is smooth, soft and shiny.

EXAMPLE 3

A shampoo composition according to the invention was prepared with the following composition (AM means Active Material):

| | |
|---|---|
| (C8/C10/C12/C14)Alkyl polyglycoside-(1.4) as an aqueous solution comprising 53% of AM (Plantacare 2000 from Henkel) | 7.4 g AM |
| Sodium lauryl ether sulphate oxyethylenated with 2.2 mol of ethylene oxide as an aqueous solution comprising 70% of AM | 9.8 g AM |
| Jojoba oil | 6 g |
| Preservatives | q.s. |
| Citric acid.1H2O q.s | pH 5.5 |
| Demineralized water q.s. for | 100 g |

Hair was washed using this composition. It was subsequently rinsed with running water.

Before drying, it is found that the hair is very soft in the wet state and satisfactorily disentangles. After drying, it is found that the hair is smooth, soft and shiny.

EXAMPLE 4

A shampoo composition according to the invention was prepared with the following composition (AM means Active Material):

| | |
|---|---|
| (C8/C10/C12/C14)Alkyl polyglycoside-(1.4) as an aqueous solution comprising 53% of AM (Plantacare 2000 from Henkel) | 7.4 g AM |
| Sodium lauryl ether sulphate oxyethylenated with 2.2 mol of ethylene oxide as an aqueous solution comprising 70% of AM | 9.8 g AM |
| Cocoyl betaine as an aqueous solution comprising 30% of AM | 2.1 g AM |
| Avocado oil | 6 g |
| Mixture of cetyl alcohol and of 1-(hexadecyloxy)-2-octadecanol | 2 g |
| Coconut acid monoisopropanolamide | 0.8 g |
| Preservatives, fragrance | q.s. |
| Citric acid.1H2O q.s | pH 5.5 |
| Demineralized water q.s. for | 100 g |

Hair was washed using this composition. It was subsequently rinsed with running water.

Before drying, it is found that the hair is very soft in the wet state and satisfactorily disentangles. After drying, it is found that the hair is smooth, soft and shiny.

EXAMPLE 5

A shower gel composition according to the invention was prepared with the following composition (AM means Active Material):

| | |
|---|---|
| (C8/C10/C12/C14)Alkyl polyglycoside-(1.4) as an aqueous solution comprising 53% of AM (Plantacare 2000 from Henkel) | 8 g AM |
| Sodium lauryl ether sulphate oxyethylenated with 2.2 mol of ethylene oxide as an aqueous solution comprising 70% of AM | 10 g AM |
| Cocoyl betaine as an aqueous solution comprising 30% of AM | 5 g AM |
| Avocado oil | 4 g |
| Hydroxyethylcellulose crosslinked with epichlorohydrin and quaternized with trimethylamine (JR 400 from Union Carbide) | 0.3 g |
| Mixture of cetyl alcohol and of 1-(hexadecyloxy)-2-octadecanol | 2 g |
| Coconut acid monoisopropanolamide | 0.8 g |
| Glycerol | 3 g |
| Preservatives, fragrance | q.s. |
| Citric acid.1H2O q.s | pH 5.5 |
| Demineralized water q.s. for | 100 g |

Skin washed with this shower gel exhibits a protective film, is well moisturized and is very soft.

What is claimed is:

1. A conditioning and detergent foaming composition, comprising, in an aqueous medium:
   (A) at least one non-volatile vegetable oil,
   (B) at least one anionic sulphate surface-active agent,
   (C) at least one non-ionic alkyl glycoside surface-active agent, the (B)/(C) ratio by weight being less than or equal to 2:1.

2. The composition according to claim 1 wherein said at least one non-volatile vegetable oil is chosen from sunflower oil, avocado oil, jojoba oil, maize oil, sweet almond oil, soybean oil, cucumber oil, grape seed oil, sesame oil, hazelnut oil, palm oil, castor oil, walnut oil, cashew nut oil and purcellin oil.

3. The composition according to claim 1 wherein said at least one non-volatile vegetable oil results from dicotyledonous plants.

4. The composition according to claim 3 wherein said at least one non-volatile vegetable oil is chosen from avocado oil and jojoba oil.

5. The composition according to claim 1 wherein said at least one non-ionic alkyl glycoside surface-active agent is chosen from compounds of formula (I):

$$R_1-O-(R_2O)_t-(G)_v \qquad (I)$$

in which:
   $R_1$ is chosen from saturated and unsaturated, linear and branched, alkyl radicals comprising from 8 to 24 carbon atoms, and alkylphenyl radicals wherein the alkyl radical is chosen from linear and branched alkyl radical comprising from 8 to 24 carbon atoms;
   $R_2$ is chosen from alkylene radicals comprising from 2 to 4 carbon atoms;
   G is chosen from reduced sugars comprising from 5 to 6 carbon atoms;
   t ranges from 0 to 10; and,
   v ranges from 1 to 15.

6. The composition according to claim 5 wherein $R_1$ is chosen from saturated and unsaturated, linear and branched, alkyl radicals comprising from 8 to 14 carbon atoms, t is 0, G is glucose and v ranges from 1 to 4.

7. The composition according to claim 1 wherein said at least one anionic sulphate surfactant is chosen from salts of:
   alkyl sulphates,
   alkyl ether sulphates,
   alkylamido ether sulphates,
   alkylaryl ether sulphates, and alkylethersulphosuccinates.

8. The composition according to claim 7 wherein said alkyl radicals comprise from 8 to 24 carbon atoms and said aryl radical is chosen from phenyl and benzyl groups.

9. The composition according to claim 7 wherein said at least one anionic sulphate surfactant is chosen from salts of alkyl sulphates and alkyl ether sulphates.

10. The composition according to claim 1 wherein said composition further comprises at least one amphoteric surface-active agent.

11. The composition according to claim 10 wherein said at least one amphoteric surface-active agent is chosen from betaines.

12. The composition according to claim 1 wherein said (B)/(C) weight ratio ranges from 0.1:1 to 1.8:1.

13. The composition according to claim 1 wherein said at least one non-volatile vegetable oil ranges from 0.1 to 20% by weight with respect to the total weight of the composition.

14. The composition according to claim 1 wherein said at least one anionic sulphate surfactant ranges from 1 to 20% by weight with respect to the total weight of the composition.

15. The composition according to claim 1 wherein said at least one non-ionic alkyl glycoside surface-active agent ranges from 0.5 to 15% by weight with respect to the total weight of the composition.

16. The composition according to claim 10 wherein said at least one amphoteric surface-active agent is present in concentrations from 0.5 to 10% by weight with respect to the total weight of the composition.

17. The composition according to claim 1 wherein said elements (B) and (C) range from 3 to 50% by weight with respect to the total weight of the composition.

18. The composition according to claim 1, further comprising at least one additional detergent element, wherein said elements (B) and (C) and said at least one additional detergent element range from 3 to 50% by weight with respect to the total weight of the composition.

19. The composition according to claim 1 wherein said composition further comprises at least one adjuvant chosen from cationic surfactants, anionic, non-ionic, cationic, and amphoteric polymers, proteins, ceramides, pseudoceramides, hydroxy acids, vitamins, panthenol, volatile and non-volatile silicones, soluble and insoluble silicones, moisturizing agents, antidandruff agents, antiseborrhoeic agents, sunscreening agents, and agents for combatting free radicals.

20. The composition according to claim 19 wherein said cationic polymers are chosen from quaternary cellulose ether derivatives, diallyldimethylammonium salt homopolymers, copolymers of diallyldimethylammonium salt and acrylamide, cationic polysaccharides, optionally crosslinked homopolymers of (meth) acryloyloxyethyltrimethylammonium salt, and optininally crosslinked copolymers of (meth) acryloyloxyethyltrimethylammonium salt and Hexadimethrine chloride.

21. The composition according to claim 19 wherein said at least one adjuvant is chosen from cationic polymers ranging from 0.001% to 10% by weight of the total weight of the composition.

22. The composition according to claim 21 wherein said at least one adjuvant is chosen from cationic polymers from 0.005% to 5% by weight of the total weight of the composition.

23. The composition according to claim 22 wherein said at least one adjuvant is chosen from cationic polymers ranging from 0.01% to 3% by weight of the total weight of the composition.

24. The composition according to claim 20 wherein said copolymers of diallyldimethylammonium salt and acrylamide are chloride copolymers.

25. A process for washing and conditioning a keratinous substance, comprising:

wetting said keratinous substance, applying to said keratinous substance an effective amount of a composition comprising, in an aqueous medium:

(A) at least one non-volatile vegetable oil, (B) at least one anionic surfactant of sulphate type, (C) at least one non-ionic alkyl glycoside surface-active agent, wherein the ratio by weight of (B)/(C) is less than or equal to 2, and rinsing said keratinous substance with water, after an optional resting time.

26. A process for simultaneously caring for and washing a keratinous substance, comprising:

wetting said keratinous substance, applying to said keratinous substance an effective amount of a composition comprising, in an aqueous medium:

(A) at least one non-volatile vegetable oil, (B) at least one anionic surfactant of sulphate type, (C) at least one non-ionic alkyl glycoside surface-active agent, wherein the ratio by weight of (B)/(C) is less than or equal to 2, and rinsing said keratinous substance with water, after an optional resting time.

27. A shampoo composition for washing and condition hair comprising, in an aqueous medium:

(A) at least one non-volatile vegetable oil, (B) at least one anionic sulphate surface-active agent, (C) at least one non-ionic alkyl glycoside surface-active agent, the (B)/(C) ratio by weight being less than or equal to 2:1.

28. A shower gel composition for washing and conditioning hair or skin comprising, in an aqueous medium:

(A) at least one non-volatile vegetable oil, (B) at least one anionic sulphate surface-active agent, (C) at least one non-ionic alkyl glycoside surface-active agent, the (B)/(C) ratio by weight being less than or equal to 2:1.

29. A foam bath composition for washing and conditioning hair or skin comprising, in an aqueous medium:

(A) at least one non-volatile vegetable oil, (B) at least one anionic sulphate surface-active agent, (C) at least one non-ionic alkyl glycoside surface-active agent, the (B)/(C) ratio by weight being less than or equal to 2:1.

30. A foaming make-up removal composition, comprising, in an aqueous medium:

(A) at least one non-volatile vegetable oil, (B) at least one anionic sulphate surface-active agent, (C) at least one non-ionic alkyl glycoside surface-active agent, the (B)/(C) ratio by weight being less than or equal to 2:1.

* * * * *

UNITED STATES PATENT AND TRADEMARK OFFICE
CERTIFICATE OF CORRECTION

PATENT NO.   : 6,156,297
DATED        : December 5, 2000
INVENTOR(S)  : Veronique Maurin et al.

Page 1 of 1

It is certified that error appears in the above-identified patent and that said Letters Patent is hereby corrected as shown below:

Claims,

Claim 20, column 11,
Line 50, change "optinionally" to -- optionally --.

Claim 27, column 12,
Line 31, change "condition" to -- conditioning --.

Signed and Sealed this

Twenty-fifth Day of September, 2001

*Attest:*

*Nicholas P. Godici*

NICHOLAS P. GODICI
*Attesting Officer*   *Acting Director of the United States Patent and Trademark Office*